(12) United States Patent
Denk

(10) Patent No.: US 6,231,495 B1
(45) Date of Patent: May 15, 2001

(54) RADIATION EMITTING, ELASTIC HOSE FOR THE ENDOVASCULAR THERAPY

(75) Inventor: Roman Denk, Weldenstetten (DE)

(73) Assignee: Universitat Karlsruhe, Karlsruhe (DE)

( * ) Notice: Subject to any disclaimer, the term of this patent is extended or adjusted under 35 U.S.C. 154(b) by 0 days.

(21) Appl. No.: 09/403,595

(22) PCT Filed: Apr. 27, 1998

(86) PCT No.: PCT/EP98/02482

§ 371 Date: Dec. 27, 1999

§ 102(e) Date: Dec. 27, 1999

(87) PCT Pub. No.: WO98/48850

PCT Pub. Date: Nov. 5, 1998

(30) Foreign Application Priority Data

Apr. 26, 1997 (DE) .............................................. 197 17 775

(51) Int. Cl.⁷ ...................................................... A61N 5/00
(52) U.S. Cl. ...................................................... 600/1; 600/3
(58) Field of Search .............................. 600/1, 2, 3, 4–8; 424/1.11; 264/5; 252/625

(56) References Cited

U.S. PATENT DOCUMENTS

| | | |
|---|---|---|
| 5,213,561 | 5/1993 | Weinstein et al. . |
| 5,302,168 | 4/1994 | Hess . |
| 5,674,192 | 10/1997 | Barry et al. . |

FOREIGN PATENT DOCUMENTS

| | | |
|---|---|---|
| 196 00 669 | 9/1997 | (DE) . |
| 0 819 446 | 1/1998 | (EP) . |
| 0 853 957 | 7/1998 | (EP) . |
| 97 19706 | 6/1997 | (WO) . |
| 97 33628 | 9/1997 | (WO) . |
| 97 38730 | 10/1997 | (WO) . |

OTHER PUBLICATIONS

Future perspectives in coronary stenting!, Hernandez et al., Rev Esp Cardiol, 1997, 50 Suppl 2 P95–106.

"Endovascular stents: a 'break through technology', future challenges", Violaris et al., Int J Card Imaging, Feb. 1997, 13(1) P3–13.

"Restenosis postangioplasty: Role of local drug delivery on its prevention", Badimon et al., Cardiovascular Risk Factors, 1996, 6/6 (318–327).

Primary Examiner—Cary O'Connor
Assistant Examiner—Brian Szmal
(74) Attorney, Agent, or Firm—McDermott, Will & Emery

(57) ABSTRACT

The present invention is related to a radiation emitting, elastic hose for the endovascular therapy composed of at least a polymeric binder comprising at least one elastomer, wherein at least a radioisotope or a radioisotope-containing compound or a combination thereof is incorporated into the polymeric binder.

13 Claims, No Drawings

RADIATION EMITTING, ELASTIC HOSE FOR THE ENDOVASCULAR THERAPY

DESCRIPTION

The present invention is related to a radiation emitting, plastic hose for the endovascular therapy of stenoses and restenoses, a method of its preparation and its use.

The expansion of vessels and vascular systems, respectively, which are constricted or closed by tissue proliferations and/or deposits by means of an appropriate balloon catheter, abbreviated PTCA, is one of the possible forms of therapy for treating an angiostenosis or a vascular occlusion (infarct or thrombosis). It is known from results of treating stenoses by conventional, i.e. non-radioactive therapy, that up to 50% of all patients treated in this manner will suffer again within a short time from a vascular occlusion, that is, from a restenosis which makes renewed measures necessary. So-called stents of various materials are used as a supporting measure which are used quasi as support for the expanded vessel. However, it turns out that even this support is often not capable of preventing restenoses. Therefore, various attempts, from the treating of the vessels with medicaments inhibiting cell growth to the use of radioactive stents, are known for the solution of this problem. Experiments with radioactive stents and radioactive balloon catheters used with the object of reducing restenoses have been shown the therapeutic effectiveness of radioactivity.

The disadvantage of radioactive stents can be found in their grid like structure. This structure results on the one hand in a non-uniform irradiation of the surrounding tissue. On the other hand, such stents remain permanently in the body so that a rather long-term radioactive irradiation and therewith a higher integral radiation dosage must be accepted than is necessary.

In order to avoid these disadvantages, devices have been developed which radioactively irradiate the vascular section to be treated only for a few minutes to a few hours. This is achieved by applying the appropiate radiation dosage together with the balloon catheter used for the angioplasty. U.S. Pat. No. 5,213,561 discloses a balloon catheter with a radioactive guide wire. Such a solution has the disadvantage that the radioactivity is not released directly at the tissue to be treated and, in addition, is also screened by the balloon. For this reason either β-emitters in very high activities or γ-emitters are used in such devices. Both are disadvantageous, since the activities should be held as low as possible. Further, γ-radiation penetrates even into rather low-lying tissue layers which should actually not be irradiated. In addition, γ-radiation is absorbed considerably more poorly than β-radiation and, therefore, exhibits a lower therapeutic action. Moreover, the use of high activities or the use of γ-emitters results in a significant technical and financial expense for the appropriate safety measures, that is, screenings for the personnel, etc. A further disadvantage is to be found in the very difficult centering of the radioactive guide wire. This centering within the catheter balloon must be exactly assured in order to achieve a uniform irradiation of the vascular section concerned, since otherwise the efficiency of this intervention becomes less, as already described for stents.

It has furthermore been suggested that a radioactive liquid be filled into a special catheter and used as a source for the radioactive radiation, which radioactivity is brought in this manner to the location to be treated. In addition to the disadvantages already cited above caused by the screening of the radioactive source by the balloon skin, this procedure involves other disadvantages which reside in particular in the poorer ability to be manipulated (e.g. leakages, spilling of the liquid, etc.) and basically represent a greater risk in comparison to a solid radioactive source.

A further possibility is constituted by the fastening of radioactive materials or isotopes to the balloon surface. U.S. Pat. No. 5,302,168 describes the fastening of radioactive strips to the balloon skin. However, no statements about the type of fastening or the layer thickness can be determined, so that a permanent adhesion of these strips to the surface is possibly not present here. Finally, even this solution has the disadvantage that the tissue is not uniformly irradiated.

The radioactive balloon catheter described in DE 195 01 154 represents an advance over the solutions already discussed. With respect to DE 195 01 154, the radioactivity is applied permanently in the form of nuclides in, to or on the balloon wall, that is, permanently connected to this wall and forms a homogeneous distribution of the radioactivity there, which is important for a high therapeutic efficiency. However, there are also problems in this instance, particularly with respect to the manufacture of these catheters. From the material-pro-cessing standpoint it is very expensive to first produce the catheter with the balloon, then to dope or coat the balloon radioactively and only then to sterilize it. Further, the isolated manufacture of a balloon provided with radioactive material and its subsequent insertion into a complete catheter is very difficult to perform from a material-processing standpoint. Methods are also used in the production of radioactive stents which comprise the implantation of radioactive material by the bombardment of metallic stents with the corresponding nuclide. However, in the field of plastics, such methods can result in changes of the plastic-elastic properties with the danger of contamination of the patient. In addition, the corresponding production method is very time-intensive. Moreover, analogously to the production methods of stents, an irradiation of the plastic materials which are doped or provided with a metallic layer in appropiate reactors is excluded. On account of the radiation fluxes (thermal neutron flux, etc.) prevailing in the respective reactors and the temperature conditions, the elastic properties of the plastics would degrade and would thus no longer be suitable for use.

Moreover, procedures which describe an application of the radioactive source to the outside of the catheter balloon without a covalent chemical bond of the particular radioactive material involve the risk of so called "Teachings". This signifies a leaching out of the components which have been added to the balloon from the balloon skin and the associated risk of contamination of the patient.

Also, the application of a layer with a polymeric film which can be cross-linked by light and is compounded with radioisotopes is not uncritical, because it is necessary to produce an elasticity which is comparable to the balloon wall, the elasticity and tensile resistance of which must not be influenced by the introduction of softeners.

The problems presented show that there is a great need in the area of the endovascular therapy of stenoses for a device which is simple to manipulate and makes possible the efficient and reliable use of radioactive radiation, especially the use of β-radiation, which is therapeutically considerably more effective and simpler to manage. Therefore, the technical problem underlying the present invention is to provide a device which permits a homogeneous and efficient endovascular therapy, preferably radiotherapy, before, during and after a balloon dilation and which does not have the disadvantages cited above, as well as a method of its production, wherein the production of this device should be able to take place separately from the production of the catheter for reasons of cost and also on account of the strict legal regulations with respect to the handling of radioactive substances.

The solution to the afore-mentioned problem is achieved by the embodiments characterized in the claims. In particular, there is provided a radiation emitting, elastic hose for the endovascular therapy composed of at least a polymeric binder comprising at least one elastomer, wherein at least a radioisotope or a radioisotope-containing compound or a combination thereof is incorporated into the polymeric binder.

Further, there is provided a method for the preparation of the radiation emitting, elastic hose for the endovascular therapy according to the present invention, wherein the radioisotope and/or the radioisotope-containing compound is/are incorporated into the polymeric binder during the polymerization step of the polymeric binder. To this extent, the hose according to the present invention can be used advantageously as a covering for catheters, preferably perfusion catheters, and stents.

In a preferred embodiment, the radioisotope incorporated into the polymeric binder is bound to the main chain of the polymeric binder by covalent bondings. In another preferred embodiment, the radioisotope-containing compound incorporated into the polymeric binder contains isotope-substituted pigments and/or radioactive microparticles. Preferably, the isotope-substituted pigments and/or radioactive microparticles have a particle size not greater than 2 nm.

In principle, all nuclides can be considered as nuclides which can be worked into the hose and which assure a homogeneous and effective irradiation of the tissue of a patient. The radioisotope can be α- and/or β- and/or γ-emitters. However, β-emitters are preferred. For example, the radioisotope can be selected from the group consisting of S-33, S-34, Se-75, I-125, Co-60, Co-55, Fe-55, P-32, P-33, Mn-52, Ta-182, Zr-96, Sr-90 and Tc-99. In particular, the short-living nuclides with a half-life of less than one month such as e.g. P-32, P-33, Tc-99, Co-55, Fe-55, Mn-52, S-33 and S-34 are advantageous in this respect, since the removal can be carried out more easily. However, even the long-living nuclides such as e.g. Sr-90, Co-60, Ta-182, Zr-96, I-125 and Se-75 can be used. This means that for the doping of the hose chemical compounds containing a radioactive isotope which will be covalently bound to the main chain of the polymeric binder, as well as isotope substituted pigments or also radioactive microparticles incorporated into the polymeric binder which can have also radiopaque properties, can be used.

The elastomer constituting the poymeric binder can be natural rubber or a synthetic rubber or a mixture thereof. The natural rubber can be selected from e.g. gutta-percha, polyisoprene or latex. The synthetic rubber can be selected from e.g. polybutadiene, polyisoprene, polychloroprene, neoprene rubber, ethylene-propylene rubber, acrylic rubber, fluorinated rubber, silicone rubber, polyurethane rubber and polyphosphor-elastomers like polyphosphazenes.

The hose according to the present invention can contain further biocompatible fillers and/or stabilizers and/or auxiliary substances, provided that properties like the elasticity will not be impaired negatively.

In order to be used, the elastic hose according to the present invention is slipped over the balloon of the balloon catheter, preferably a perfusion catheter, used. Accordingly, the length of the hose is preferably somewhat greater than that of the balloon used. The diameter of the hose can be smaller or equal to the outside diameter of the balloon. It is decisive that it can be slipped over the balloon and rests closely on the latter both in the folded-together state as well as in the expanded state. Possibilities for fixing the hose to the balloon catheter can be provided at the ends. Preferably, the hose according to the present invention has a thickening or one ore more bulges on each end. In another embodiment of the present invention, it is not necessary that the hose is open on each end. Furthermore, the fixing can also take place by means of clips of metal or of plastic. In addition, the hose can also be fastened mechanically by O-rings or devices similar to hose clamps. Likewise, the hose can be adhered at its ends to the catheter.

Radiopaque or radioactive markings can be applied to the hose which make it possible to monitor the catheter path with X-ray monitoring. The addition of appropriate radiopaque pigments can turn the hose itself in a radiopaque device which can therefore be monitored radiographically.

In addition thereto, the hose can be designed in such a manner that it contains appropriate therapeutic means such as e.g. cytostatic agents which can be released in a purposeful manner.

The great advantages of the hose according to the present invention reside in its simple manufacture as well as in its manipulation. By the hose according to the present invention, it is advantageously assured that the radioactivity comes directly in contact with the tissue to be irradiated or treated and at the same time the mechanical properties of the catheter balloon are not adversely affected. Moreover, the hose is very simple to manipulate. In addition, the production of the hose can take place separately from the catheter manufacture, which significantly reduces the safety measures and therewith also the costs. The use of the hose can take place in combination with commercial balloon catheters which can optionally be slightly modified. For example, very minimal changes in the form of one or two bulges can be made to a commercial catheter for a fastening or the hose can be adhered at its ends to the catheter. Further advantages of the hose are that neither the mechanical properties of the catheter balloon such as e.g. pressure stability or elasticity of the balloon are influenced nor are changes of the original surface of the balloon necessary.

Moreover, the working and also the manufacture of the hose according to the present invention such as e.g. the changing of the surface by coatings such as e.g. spit coating or the covalent bonding on of radioactive isotopes or changes of the mechanical properties such as e.g. the elasticity as well as other adaptations to various requirements can be carried out in a quite simple manner. Advantageously, the hose according to the present invention adapts itself in each phase of use to the form of the catheter balloon and therewith also to the form of the corresponding vascular section, thus assuring the optimal therapeutic effect.

Moreover, the problem of recycling can be solved very easily. After the PTCA the catheter together with the hose according to present invention is removed from the vessel, the catheter tip can be cut off and stored in a container of polyacryl, lead or some other screening material with an appropriate thickness where, depending on the nuclide used, the hose is either recycled or stored until the abatement of the activity.

A further advantage is offered by the option that the hose can be offered either as an individual product in addition to commercial catheters or supplied already mounted on the catheter in the factory as a component of the catheter.

The present invention is further explained by way of the following non-restricting examples.

EXAMPLE 1

Approximately 3–5% by weight of a mixture of sulfur and phosphorus-32 whose activity corresponds to approximatly 750 mCi are added to a commercial latex emulsion. After being mixed, this emulsion is filled into an appropriate mold and the vulcanization is carried out at about 130° C. The subsequent treatment is carried out according to common methods known in the art. Likewise, the parameters are known for achieving an appropriate elasticity along with high rigidity of the respective polymeric binder constituting the hose according to the present invention. A layer of surfactant, lubricant or of fat can also be applied to the outside of the finished hose in order to further improve the sliding ability of the surface. Otherwise, the surface of the hose can be further treated according to known methods in order to achieve an improved sliding ability (e.g. fatty creams, glycerol and the like).

EXAMPLE 2

2 mg of a $FePO_4/FeP^{32}O_4$ mixture are added to a 5 ml commercial latex emulsion with the activity of not exceeding 700 mCi. Approximately 3–5% by weight of sulfur are added to this emulsion and after mixing this emulsion is filled into an appropriate mold and the vulcanization is carried out at approximately 130 ° C. The subsequent treatment is carried out according to common methods known in the art. Likewise, the appropriate parameters are known for achieving an appropriate elasticity along with great rigidity of the respective polymeric binder constituting the hose according of the present invention (cf. general textbooks of polymer chemistry).

EXAMPLE 3

A pre-formed, already vulcanized, elastic hose of latex is closed at the end and filled 1 hour with a 2% radioactive solution of $HI^{125}$. The activity of the solution is approximately 700 mci. The solution is removed and the hose is dried. The hose radioactively doped in this manner with $I^{125}$ can then be drawn with the radioactive inner side over a commercial catheter, preferably a perfusion catheter, and fixed.

EXAMPLE 4

A pre-formed, thin latex hose is filled 10 minutes with a 5% radioactive solution of $I_2^{125}$ in chloroform and then closed. The activity of the solution present in the hose is approximately 700 mci. The hose is heated with the solution, as a result of which $I^{125}$ is covalently bound to the latex. After the reaction has been completed the solution is cooled down, then the solution removed and the hose dried. The hose radioactively doped in this manner with $I^{125}$ can then be drawn with the radioactive inner side over a commercial catheter, preferably a perfusion catheter, and fixed.

EXAMPLE 5

A hose manufactured according to Examples 1–4 is appropriately cut to length and adhered at the ends of a commercial catheter balloon with a commercially available two component adhesive.

EXAMPLE 6

A hose according to the present invention is prepared from elastic foam, preferably neoprene foam, and this hose is impregnatic with a cytostatic agent, drawn onto a commercial balloon catheter and fastened.

What is claimed is:

1. A radiation emitting, elastic hose for the endovascular therapy composed of at least a polymeric binder comprising at least one elastomer, wherein at least a radioisotope or a radioisotope-containing compound or a combination thereof is incorporated into the polymeric binder.

2. The hose according to claim 1, wherein the radioisotope is bound to the main chain of the polymeric binder by covalent bonding.

3. The hose according to claim 1, wherein the radioisotope-containing compound contains isotope-substituted pigments and/or radioactive microparticles.

4. The hose according to claim 3, wherein the isotope-substituted pigments and/or radioactive microparticles have a particle size not greater than 2 nm.

5. The hose according to claim 1, wherein the radioisotope emits $\alpha$- and/or $\beta$- and/or $\gamma$-radiation.

6. The hose according to claim 5, wherein the radioisotope is selected from the group consisting of S-33, S-34, Se-75, I-125, Co-60, Co-55, Fe-55, P-32, P-33, Mn-52, Ta-182, Zr-96, Sr-90 and Tc-99.

7. The hose according to claim 1, wherein the elastomer is a natural rubber or a synthetic rubber or a mixture thereof.

8. The hose according to claim 7, wherein the natural rubber is selected from gutta-percha, polyisoprene or latex.

9. The hose according to claim 7, wherein the synthetic rubber is selected from polybutadiene, polyisoprene, polychloroprene, neoprene rubber, ethylene-propylene rubber, acrylic rubber, fluorinated rubber, silicone rubber, polyurethane rubber and polyphosphor-elastomers.

10. The hose according to claim 1, wherein the hose contains further biocompatible fillers and/or stabilizers and/or auxiliary substances.

11. The hose according to claim 1, which has a thickening or a bulge on each end.

12. A method for the preparation of the radiation emitting, elastic hose for the endovascular therapy according to claim 1, wherein the radioisotope and/or the radioisotope-containing compound is/are incorporated into the polymeric binder during the polymerization step of the polymeric binder.

13. Use of the hose according to claim 1, as a covering for catheters, preferably perfusion catheters, and stents.

* * * * *